United States Patent [19]

Jeanson et al.

[11] Patent Number: 5,531,554

[45] Date of Patent: Jul. 2, 1996

[54] SELF-RETAINING MEANS FOR FASTENERS PARTICULARLY SCREWS

[75] Inventors: Jean-François Jeanson, Assenay; Jean Huppert, L'Etrat, both of France

[73] Assignee: JBS S.A., Troyes, Cedex, France

[21] Appl. No.: 336,655

[22] Filed: Nov. 4, 1994

[30] Foreign Application Priority Data

Nov. 5, 1993 [FR] France .................... 93 13165

[51] Int. Cl.⁶ .............. F16B 23/00; F16B 39/00
[52] U.S. Cl. .......... 411/399; 411/107; 411/533; 411/999
[58] Field of Search .................. 411/107, 337, 411/386, 387, 399, 424, 533, 970, 999

[56] References Cited

U.S. PATENT DOCUMENTS

| 3,782,437 | 1/1974 | Seckerson | 411/107 |
| 3,789,725 | 2/1974 | Lindstrom | 411/387 |
| 4,274,460 | 6/1981 | Egner | 411/424 |
| 4,509,890 | 4/1985 | Hill . | |
| 4,652,018 | 3/1987 | Boghosian | 411/999 X |

FOREIGN PATENT DOCUMENTS 664642  1/1952  United Kingdom .

Primary Examiner—Neill R. Wilson
Attorney, Agent, or Firm—Spencer & Frank

[57] ABSTRACT

A fastener for insertion through aligned holes of two components to be secured to one another by the fastener. The fastener includes a shaft portion having an end; a fastener head disposed at said end; and a retaining arrangement for maintaining the fastener captive by the components. The retaining arrangement includes a conical collar situated between the shaft portion and the fastener head. Further, the conical collar surrounds the axis and has a maximum diameter base oriented toward the fastener head. The conical collar is provided with radial recesses. The retaining arrangement also has a neck part surrounding the shaft axis and disposed between the fastener head and the conical collar.

5 Claims, 1 Drawing Sheet

SELF-RETAINING MEANS FOR FASTENERS PARTICULARLY SCREWS

BACKGROUND OF THE INVENTION

The invention relates to self-retaining means for fasteners particularly to screws.

Up to now, the only possibility to make sure that a fastener remains in a plate is to secure it with a relatively thick element, or to apply such type of screws wherein a neck part is below the head of the screw and the neck part is longer than the thickness of the plate wherein upon introducing the screw into a bore of the plate, the axis of the screw generally moves out from the geometrical axis of the bore, which hinders separation of the screw.

There is, however, still a real danger that the geometrical axis of the bore and that of the screw coincide and such a position, even if only for a short time, permits the screw to drop out, which is always undesirable but it is even dangerous in the field of surgery.

SUMMARY OF THE INVENTION

It is therefore the object of the present invention to avoid these inconveniences. This invention, as it is characterized, solves the problem to provide a means which is an integral part of a fastener, which makes impossible to remove it from the element which it has the task of fixing.

The self-retaining fastener, according to the present invention for securing an element to another element is essentially characterized in that the fastener is provided with a conical collar, the maximum diameter base of which is facing the head of the fastener, there are radial notches in the collar and a neck part is arranged between the collar and the head.

The diameter of the base of the collar is greater than that of the bore receiving the fastener in one of the elements to be secured to the other one.

According to one embodiment, the radial notches of the collar may be of triangular shape.

In another preferred embodiment, the radial notches of the collar are simple slots.

The neck part between the collar and the head is of conical shape wherein the cone angle as well as the direction of the cone is the same as that of the collar.

A conical recess is provided in the base of the collar.

The advantages of the invention are essentially that the fastener cannot be removed from an element after it has been inserted into the bore of the element and there is no need to apply any tool or special device for introducing the fastener into the bore, except the normal tool applied for that type of fasteners.

Other characteristics and advantages will be apparent in the following description of a self-cutting screw provided with a milled head, used in the field of surgery for fixing a cervical plate, as a non-limiting example of the invention.

DESCRIPTION OF THE PREFERRED EMBODIMENTS

The Figures show a self-cutting screw (fastener) 10 provided with a head 20, a conical collar 30 with radial notches 31 and a neck part 40 which is conical as well.

Figure 1:
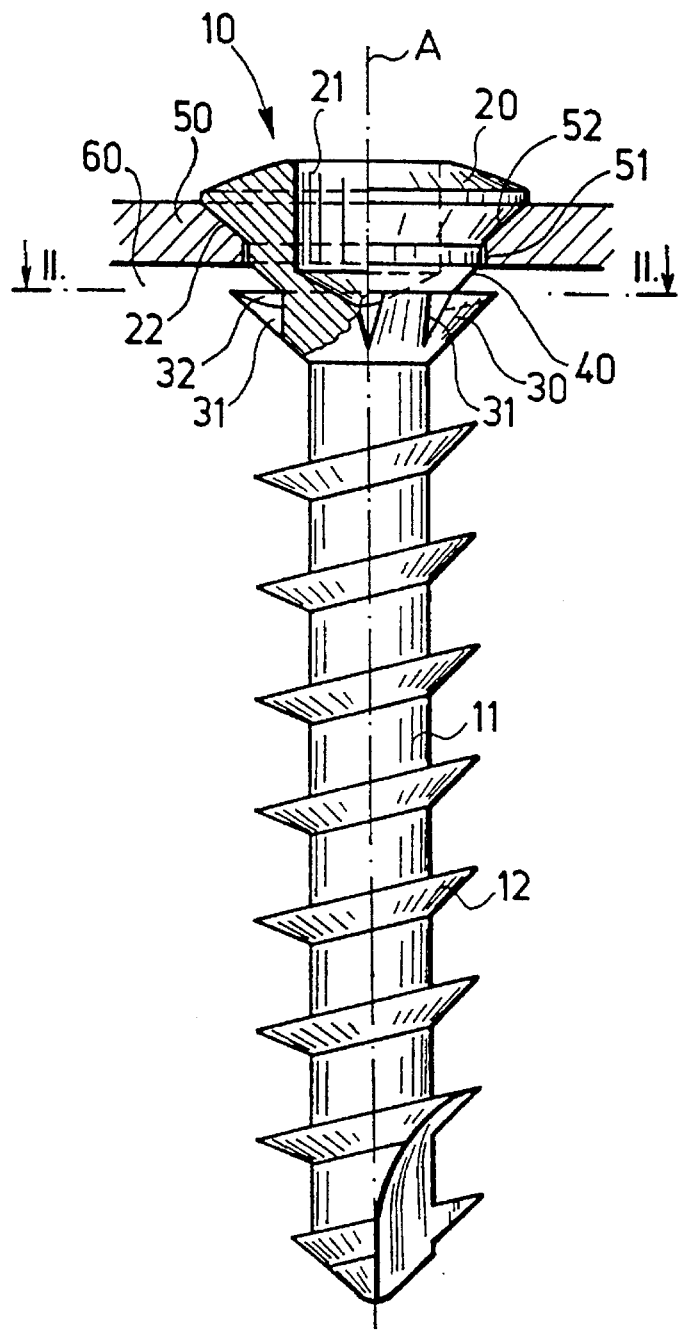
FIG. 1 is an elevational view of a screw according to the invention, partly in section.
Figure 2:
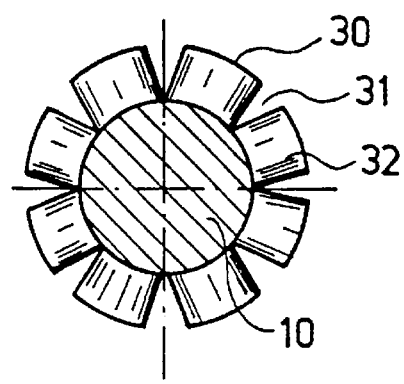
FIG. 2 is a sectional view taken along line II—II of FIG. 1.

As seen in FIGS. 1 and 2, the self-retaining fastener 10 includes a shaft portion 11 having an axis A and carrying a self-cutting thread 12. The self-retaining fastener is an integral part of the screw and consists of a conical collar 30 surrounding the axis A and being provided with radial notches (recesses) 31 arranged along the periphery of the conical collar 30 at equal distances in order to allow a gradual decreasing of the maximum diameter of the collar 30 to enable the screw to pass through the bore 51 of plate 50 in the first step of securing the elements together. The gradual decreasing of the diameter is also promoted by a conical recess 32 in the base of the conical collar 30.

Accordingly, when screw 10 is screwed into the second element by applying a wrench in the hexagonal opening 21, plate 50 is pushed first against the face of the second element 60 when the conical collar 30 reaches a conical section 52 of bore 51 in the first element and from this position on, the maximum diameter of collar 30 gradually decreases—that is, the collar 30 undergoes a radially constrictive deformation—until it is pushed through bore 51 due to the cooperation of the notches 31 and the conical recess 32. Thereafter the conical outer surface 22 of head 20 presses again plate 50 to the second element via conical section 52 of the bore 51.

In this way, screw 10 remains captive and thus cannot be removed from the first element 50, unless a device is applied which can decrease the maximum diameter of collar 30 until it is smaller than that of the bore 51 of the plate.

Different kinds of screws can be produced by varying the distance between the conical collar 30 and the head 20 of the screw 10, for use in plates 50 of different thicknesses and the extent of pivoting the screw in bore 51 can be changed in the same way. This may be important when inaccuracies in the arrangement of the bores or other peculiarities of the second element 60 should be taken into consideration or should be compensated for.

Figure 3:
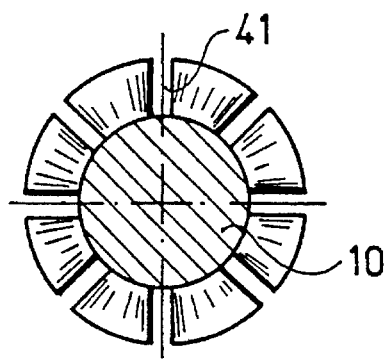
FIG. 3 is a view similar to FIG. 2, illustrating a variant.

Notches 31 of the conical collar 30 are of triangular shape according to the embodiment shown in FIG. 2. As shown in FIG. 3, simple slots 41 all having parallel side walls, however, may have the same effect, if they are wide enough to allow the required decrease of the maximum diameter.

The present invention may therefore be applied for conventional screws, threaded pins, staybolts as well as rods threaded at both ends. It can also be applied, with minor modifications, for nuts, rendering them self-retaining.

We claim:

1. A fastener for insertion through aligned holes of two components to be secured to one another by the fastener, comprising (a) a shaft portion having an end;

(b) a fastener head disposed at said end; and (c) retaining means for maintaining the fastener captive by the components; said retaining means including (1) a conical collar being situated between said shaft portion and said fastener head; said conical collar surrounding said axis and having a maximum diameter base oriented toward said fastener head; said conical collar having radial recesses; and (2) a conical neck part surrounding said axis and disposed between said fastener head and said conical collar; said conical collar and said conical neck part having cone angles of identical magnitude and orientation.

2. A fastener for insertion through aligned holes of two components to be secured to one another by the fastener, comprising (a) a shaft portion having an end;

(b) a fastener head disposed at said end; and (c) retaining means for maintaining the fastener captive by the components; said retaining means including (1) a conical collar having radial recesses and being situated between said shaft portion and said fastener head; said conical collar surrounding said axis and having a maximum diameter base oriented toward said fastener head; said base being provided with a conical recess; and (2) a neck part surrounding said axis and disposed between said fastener head and said conical collar.

3. The fastener as defined in claim 2, wherein said radial recesses are triangular.

4. The fastener as defined in claim 2, wherein said radial recesses are defined by parallel-extending side walls of said conical collar.

5. The fastener as defined in claim 2, wherein said shaft portion is a screw shaft; further comprising a self-cutting thread carried on said screw shaft.

* * * * *